United States Patent [19]

Stammer

[11] Patent Number: 4,954,158
[45] Date of Patent: Sep. 4, 1990

[54] 2,3-METHANOPROLINE

[75] Inventor: Charles H. Stammer, Athens, Ga.

[73] Assignee: University of Georgia Research Foundation, Inc., Athens, Ga.

[21] Appl. No.: 285,542

[22] Filed: Dec. 15, 1988

Related U.S. Application Data

[63] Continuation-in-part of Ser. No. 41,642, Apr. 22, 1987, which is a continuation of Ser. No. 879,842, Jun. 26, 1986, which is a continuation of Ser. No. 636,091, Aug. 3, 1984, which is a continuation-in-part of Ser. No. 523,080, Aug. 16, 1983.

[51] Int. Cl.$^5$ .................... A01N 43/38; C07D 209/52
[52] U.S. Cl. .......................................... 71/76; 71/95; 548/452
[58] Field of Search ................... 548/452, 455; 71/76, 71/95

[56] References Cited

U.S. PATENT DOCUMENTS 3,313,842  4/1967  Kaiser et al.
4,591,598  5/1986  Urbach .............................. 548/452
4,629,784  12/1986  Stammer.

OTHER PUBLICATIONS

Arenal, Bernabe, Fernandez Alveraz, Izquierdo, and Penades, *J. Heterocyclic. Chem.*, 20, 607 (1983).
Bernabe, Cuevas, and Fernandez Alveraz, *Eur. J. Med. Chem.*, Chemica Theraputica, 14 (1), 33 (1979).
Bernabe, Cuevas, and Fernandez Alveraz, "A New Synthesis of 1-Amino-2-Arylcyclopropanecarboxylic Acids", *Synthesis* 3, 191 (1977).
Bernabe, Fernandez, and Fernandez Alveraz, *Anales de Quimica*, 75, 977 (1979).
Bernabe, Fernandez Alveraz, and Ullate, "Derivatives of Cyclopropane", *Anales de Quimica*, 1005 (1972).
Bregovec and Jakoveic, *Monatshete Fur. Chemie*, 103, 288 (1972).
Elkaschef, Abdel-Megid, and Yassin, *Journal F. Prac. Chemie.*, Band 316, Heft 3 (1974), S. 363-368.
Fowden and Smith, *Phythochemistry*, 8, 437 (1969).
Fujimoto, Irreverre, Karle, Karle, and Whitkop, "Synthesis and X-Ray Analysis of Cis-3,4-Methanoline-L-Proline, The New Natural Amino Acid from Horse Chestnuts, and Its Trans Isomer", *J. Am. Chem. Soc.* 93:14, 3471 (1971).
Grouiller, Nioche, Varailler, Rouche, and Pacheco, *Eur. J. Med. Chem.*, Chemica Theraputica, 15 (2), 139 (1980).
Hanzlik, *J. Am. Chem. Soc.* 104, 2048 (1982).
Horikawa, Nishitana, Iwosaka, and Inoue, *Tet Letters* 24 (21), 2193 (1983).
Ichihara, Shiraishi, Sakamura, "Partial Synthesis and Stereochemistry of Coronatine", *Tet. Letters* No. 3, 269 (1977) and *Tet. Letters* No. 4, 365 (1979).
Ichihara, Shiraishi, Sato, Sakamura, Nishimyama, Sakai, Furusaki, and Matsumoto, "The Structure of Coronatine", *J. Am. Chem. S.* 99:2, 636 (1977).
Jung and Hudspeth, "Total Synthesis of (±)-Coronafacic Acid: Use of an Ionic Oxy-Cope Rearrangements on Aromatic Substrates in Synthesis", *J. Am. Chem. S.* 102:7, 2463 (1980).
Kimura and Stammer, "Resolution and Deblocking of Racemic N-(Benzyloxycarbonyl) Cyclopropylphenylalanine", *J. Org. Chem.* 48, 2440 (1983).
King, University of Georgia, Ph.D. Thesis, 1981.
King, Riordan, Holt, and Stammer, "Synthesis of Racemic (E)- and (Z)-1-Amino-2-Phenylcyclopropane Carboxylic Acid: (E)- and (Z)-(Cyclopropylphenylalanine)", *J. Org. Chem.* 47, 3270 (1982).
Macinnes, Nonhanbel, Orszulik, and Suckling, *J. Chem. Soc. Perkin Trans I* 2777 (1983).

(List continued on next page.)

*Primary Examiner*—Christine M. Nucker
*Assistant Examiner*—Frederick F. Tsung
*Attorney, Agent, or Firm*—Kilpatrick & Cody

[57] ABSTRACT

The present invention is 2,3-methanoproline, derivatives thereof, and biologically active molecules incorporating 2,3-methanoproline. These compounds are useful as inhibitors of ethylene production in plant material, and as synthetic analogs of biologically active molecules.

7 Claims, 2 Drawing Sheets

OTHER PUBLICATIONS

Macinnes, Nonhanbel, Orszulik, and Suckling, "Latent Inhibitors. Part III. The Inhibition of Lactate Dehydrogenase and Alcohol Dehydrogenase by Propane-Containing Compounds", *J. Chem. Soc. Perkin Trans I*, 2771 (1983).

Millington and Sheppard, "Cyclopropane Amino Acids from Aesculus and Bligihia", *Phytochemistry* 8, 437 (1969).

Nishiyama, Sakai, Ezuka, Ichihara, Shiraishi, and Sakamura, "Detection of Coronatine in Halo Blite Leisons in Rye Grass", *Ann. Phytopath. Soc. Japan* 43, 219 (1977).

Pages and Burger, "1-Amino-2-(4-Imidazolyl)-Cyclopropane Carboxylic Acid", *J. Med. Chem.*, vol. 9, p. 766 (1966).

Shiraishi, Ichihara, and Sakamura, "Facile Stereoselective Synthesis of (±)-Allocoronamic Acids", *Agric. Biol. Chem.* 41 (12), 2497 (1977).

Shiraishi, Konama, Sato, Ichihara, Sakamura, Nishiyama, and Sakai, "The Structure–Activity Relationships in Coronatine Analogs and Amino Compounds Derived from (±)-Coronafacic Acid", *Agric. Biol. Chem.* 43 (8), 1753 (1979).

Stewart, "A Synthetic Approach to Peptides of O- and P-Aminobenzoic Acids", *Aust. J. of Chem.* 36, 1639 (1983).

Stewart, "Peptide Synthesis with 1-Aminocyclopropane-1-Carboxylic Acid", *Aust. J. of Chem.* 34, 2431 (1981).

Bland, Varughese, and Stammer, "Synthesis of (E)-and (Z)-Cyclopropyl-3-Chloroalanine", *J. Org. Chem.* 49, 1634 (1984).

Suzuki, Gooch, and Stammer, "A New Synthesis of Racemic Coronamic Acid and Other Cyclopropyl Amino Acids", *Tet Letters* 24 (36), 3839 (1983).

Elrod, Holt, Mapelli, and Stammer, "Synthesis of 2,3-Methano-Glutamic and -Pyroglutamic Acid", *J. Chem. Soc., Chemical Communications* 252 (1988).

Bell, Qureshi, Pryce, Jansen, Lemke, and Clardy, "2,4-Methanoproline(2-Carboxy-2,4-Methanopyrrolidine) and 2,4-Methanoglutamic Acid (1-Amino-1,-3-Dicarboxycyclobutane) in Seeds of *Ateleiaerbert Smithii* Pittier (Leguminosae)", J. Am. Chem. Soc. 102:4 (1980).

fig. 1 fig. 2

2,3-METHANOPROLINE

This application is a Continuation-in-Part of U.S. Ser. No. 041,642, filed Apr. 22, 1987 by Charles H. Stammer, entitled "The Synthesis of Cyclopropyl Amino Acids and Peptides", which is a Continuation of U.S. Ser. No. 879,842, filed by Charles H. Stammer on June 26, 1986, which is a Continuation of U.S. Ser. No. 636,091, filed by Charles H. Stammer on Aug. 3, 1984, which is a Continuation-in-Part of U.S. Ser. No. 523,080, filed by Charles H. Stammer on Aug. 16, 1983, entitled "The Synthesis of Cyclopropane Amino Acids."

This invention relates to biochemistry, and in particular to new proline derivatives.

BACKGROUND OF THE INVENTION

U.S. Pat. No. 4,629,784 to Stammer describes the synthesis of cyclopropyl amino acids from dehydroalanine, and the synthesis of peptides containing cyclopropyl amino acids. The patent is a continuation of U.S. Ser. No. 523,808, to which this invention claims priority.

Several amino acids containing cyclopropyl rings exist in nature. The simplest cyclopropyl amino acid, 1-aminocyclopropane-1-carboxylic acid (ACC) has been discovered in the fruit of the perry pear and the cowberry. Burroughs, *J. Sci. Food Agric.* 11 14 (1960). It is now known that ACC is a biological precursor to ethylene in plants.

Coronatine, which induces phytotoxic lesions on the leaves of Italian rye-grass and hypertrophic growth of potato tuber tissue, is the amide of coronafacic acid with coronamic acid (1-amino-1-carboxy-2-ethyl-cyclopropane). Coronatine has been synthesized by various groups in whole or part. Shiraishi, Ichihara, and Sakamura, "Facile Stereoselective Synthesis of (±)-Allocornonamic Acids", *Agric. Biol. Chem.* 41 (12), 2497 (1977) describe the stereoselective synthesis and optical resolution of (±)-Allocoronamic Acid. See also Shiraishi, Konoma, Sato, Ichihara, Sakamura, Nishiyama, and Sakai, "The Structure-Activity Relationships in Coronatine Analogs and Amino Compounds Derived From (+)-Coronafacic Acid", *Agric. Biol. Chem.* 43 (8), 1753 (1979); Ichihara, Shiraishi, Sakamura, Tet Letters No. 3, 269 (1977) and *Tet Letters* No. 4, 365 (1979); Suzuki, Gooch, and Stammer, "A New Synthesis of Racemic Coronamic Acid and Other Cyclopropyl Amino Acids", *Tet Letters* 24 (36), 3839 (1983); Jung and Hudspeth, "Total Synthesis of (±)-Coronafacic Acid: Use of an Ionic Oxy-Cope Rearrangements on Aromatic Substrates in Synthesis", *J. Am. Chem. S.* 102:7, 2463 (1980).

Shiraishi, et al., in "The Structure-Activity Relationships in Coronatine Analogs and Amino Compounds Derived From (+)-Coronafacic Acid", *Agric. Biol. Chem.* 43 (8), 1753 (1979), describe the synthesis of several coronatine analogs, and the effect of varying the substituents of coronatine on the hypertrophy responsive of potato tubers. Shiraishi, et al. conclude that the presence of the carboxyl group and the configuration at the α-carbon atom in the amino acid are closely related to the activity of the peptide. However, the cyclopropane ring in coronatine was found to have no effect on the biological activity, as indicated by the comparison of the biological activity of 1-N-coronafacoylaminocyclopropane-L-isoleucine and N-coronafacoyl-D-isoleucine.

Cyclopropylphenylalanine and its derivatives have also been synthesized and studied. King, Riordan, Holt, and Stammer, in an article entitled "Synthesis of Racemic (E)- and (Z)-1-Amino-2-Phenylcyclopropane Carboxylic Acid, (E)- and (Z)-(Cyclopropylphenylalanine)", *J. Org. Chem.* 47, 3270 (1982), describe the synthesis of both E and Z isomers of D-L-cyclopropylphenylalanine. See also Stephen Wayne King, 1981 University of Georgia Ph.D Thesis. Kimura and Stammer, in "Resolution and Deblocking of Racemic N-(Benzyloxycarbonyl) Cyclopropylphenylalanine", *J. Org. Chem.* 48, 2440 (1983), report the isolation of the E-diastereomer of cyclopropylphenylalanine from a racemic mixture of Z and E. See also Suzuki, Kumar, and Stammer, "Use of a New Protecting Group in an Attempted Synthesis of Cyclopropyl Dihydroxyphenylalanine", *J. Org. Chem.* 48, 4769 (1983).

Additional examples of naturally occurring cyclopropyl amino acids include the diastereomers of α-(2-carboxy-cyclopropyl)-glycine cyclopropyl)-glycine and cis-3,4-methano-L-proline isolated from *Aesculus parviflora* and *Bliqhia saoida*. Fowden, et al., Phytochemistry, 8, 437 (1969).

Fujimoto, Irreverre, Karle, Karle, and Whitkop, in "Synthesis and X-Ray Analysis of Cis-3,4-Methanoline-L-Proline, The New Natural Amino Acid from Horse Chestnuts, and Its Trans Isomer", *J. Am. Chem. Soc.* 93:14, 3471 (1971), describe the synthesis of cis- and trans-3,4-methano-L-proline. Fujimoto, et al. established by x-ray crystallography that the bicyclic system approaches a boat conformation both in the cis and the trans configuration. They determined that the boat conformation of cis-3,4-methanoline-L-proline is associated with the compound's effect as a powerful competitor for proline in the permease system. 2-Piperidine-carboxylic acid (D-pipecolinic acid), which has a chair conformation, is inactive in these systems.

The nitrogen atom in proline is part of a rigid saturated five membered ring. Since little rotation about the N(proline)-$C_{60}$ peptide bond is possible when proline is incorporated into a peptide chain, proline imparts rigidity to peptides. It would be of chemical and pharmaceutical interest to prepare a cyclopropyl derivative of proline in which the cyclopropane ring is connected to the α-carbon of this sterically unique amino acid.

Proline is a key amino acid in many peptide hormones due to its significant effect on the conformation of the molecule. Examples of proline containing peptides include angiotensinogen, angiotensin I, angiotensin II, saralasin, capoten, vasotec, lysinopril, bradykinin, thyrotropin releasing factor, tuftsin, and melanocyte inhibiting factor.

Angiotensinogen (alternatively called renin substrate and hypertensinogen) is the twelve amino acid peptide: Asp-Arg-Val-Tyr-Ileu-His-Pro-His-Leu-Val-Tyr. Angiotensinogen plays a part in hypertension, the elevation of systolic and/or diastolic blood pressure. Angiotensinogen is cleaved at the Leu-Val bond by renin, a blood protein, to form angiotensin I (AI). AI is an inactive peptide which is cleaved at the Phe-His bond by angiotensinase (or angiotensin converting enzyme (ACE)) to form angiotensin II (AII). ACE is found in the lung, kidney and brain. The octapeptide AII differs among animal species only in the amino acid residue in position 5, where Val is sometimes found in place of Ile. Angiotensin II is a potent vasoconstrictor which also stimulates the release of aldosterone, an adrenocortical steriod.

Angiotensin II analogues have been synthesized to block the AII receptor. One is saralasin, Sar[1]-Ala[8]-AII, in which sarcosine (N-methylglycine) is substituted for aspartic acid and alanine is substituted for the phenylalanine in AII.

There are currently at least three proline containing ACE inhibitors which prevent the conversion of AI to AII. One is capoten (captopril), 1-[(2S)-3-mercapto-2-methylpropionyl]-L-proline, manufactured by E. R. Squibb and Sons, Inc. Another is vasotec (enalapril), (S)-1-[N-[1-(ethoxycarbonyl)-3-phenylpropyl]-L-alanyl]-L-proline manufactured by Merck and Co., Inc. Enalapril is the ethyl ester prodrug of enalaprilat. The third is lysinopril, (S)-1-[N-(1-(ethoxycarbonyl)-3-phenylpropyl)-L-lysinyl]-L-proline.

Proline is also found in bradykinin, a nine amino acid peptide: Arg-Pro-Pro-Gly-Phe-Ser-Pro-Phe-Arg. Bradykinin acts on smooth muscles, dilates peripheral vessels, and increases capillary permeability. Most importantly, bradykinin is a potent pain-producing agent. Bradykininase (which is identical to ACE) degrades bradykinin in vivo.

One of the three amino acids of thyrotropin releasing hormone (TRF) (pGlu-His-Pro) is proline. TRF stimulates the synthesis and secretion of both thyroid-stimulating hormone (TSH) and prolactin (PRL). Under pathologic conditions TRH may also stimulate growth hormone (GH) production and release.

Tuftsin is a naturally occurring tetrapeptide (Thr-Lys-Pro-Arg) which has a variety of immunopotentiating properties, such as stimulation and enhancement of phagocytosis. It also exhibits antitumor and antibacterial activity.

Melanostatin, alternatively called melanocyte inhibiting factor (MIF) (L-prolyl-L-leucyl-glycinamide) mediates hypothalamic control of melanotropin, a pituitary hormone. MIF is also thought to potentiate DOPA-induced behavioral changes.

Given the prevalence and importance of proline in biological systems, it would be of great benefit to prepare $C_\alpha$-$C_\beta$ cyclopropyl derivatives of proline which may be substituted for natural proline in biologically active molecules in order to modify the properties of the molecules.

Therefore, it is an object of the present invention to prepare a derivative of proline which has a cyclopropyl group in the $C_\alpha$-$C_\beta$ postion. It is a further object of the present invention to modify biologically active molecules by substituting $C_{60}$-$C_\beta$ cyclopropyl derivatives of proline for naturally occurring proline or other amino acids in the molecule.

SUMMARY OF THE INVENTION

The present invention is a compound of the general structure wherein:
$R_1$ is H, $R_9$, $COR_3$, $CO_2R_3$, $SO_2R_3$, or $R_3CH(NH_2)CO$-;
$R_2$ is H, $R_9$, $OR_3$, OH, Cl, Br, F, I, $NH_2$, $NHR_3$, $N(R_3)_2$, benzyl, phenyl or substituted benzyl or phenyl wherein the substituents may be F, Cl, Br, I, $R_9$, $OR_9$, $NHR_9$, $N(R_9)_2$, $SR_9$, $SO_2R_9$, $COR_9$, or $CO_2R_9$;
$R_3$ is H, $R_9$, phenyl or substituted phenyl wherein the substituents may be F, Cl, Br, I, $R_9$, $OR_9$, $NHR_9$, $N(R_9)_2$, $SR_9$, $SO_2R_9$, $COR_9$, $CO_2R_9$;
$R_4$ is H, Cl, Br, I, F, $OR_8$ or OH;
$R_5$ is $R_3$ or $=O$
$R_6$ and $R_7$ are $R_3$ or $COR_3$;
$R_8$ is $R_3$, $R_3CO$, or $R_3SO_2$; and
$R_9$ is a straight, branched, or cyclic alkyl group of from $C_1$ to $C_{12}$.

2,3-Methanoproline and its derivatives inhibit ethylene production in plant material. They are also useful as intermediates in the production of modified biologically active molecules.

The compounds having the general structure set forth above can be made by a variety of techniques, for example, by reacting a diazo compound with a derivative of 2,3-dehydroproline, or by intramolecular cyclization of an N-diazoalkyl dehydroalanine derivative, followed by pyrolysis or photolysis.

These compounds have a significantly different structure than, and exhibit significantly different properties from, the cyclopropyl amino acids known to date.

DETAILED DESCRIPTION OF THE INVENTION

The present invention is a compound of the general structure wherein:
$R_1$ is H, $R_9$, $COR_3$, $CO_2R_3$, $SO_2R_3$, or $R_3CH(NH_2)CO$-;
$R_2$ is H, $R_9$, $OR_3$, OH, Cl, Br, F, I, $NH_2$, $NHR_3$, $N(R_3)_2$, benzyl, phenyl or substituted benzyl or phenyl wherein the substituents may be F, Cl, Br, I, $R_9$, $OR_9$, $NHR_9$, $N(R_9)_2$, $SR_9$, $SO_2R_9$, $COR_9$, or $CO_2R_9$;
$R_3$ is H, $R_9$, phenyl or substituted phenyl wherein the substituents may be F, Cl, Br, I, $R_9$, $OR_9$, $NHR_9$, $N(R_9)_2$, $SR_9$, $SO_2R_9$, $COR_9$, $CO_2R_9$;
$R_4$ is H, Cl, Br, I, F, $OR_8$ or OH;
$R_5$ is $R_3$ or $=O$
$R_6$ and $R_7$ are $R_3$ or $COR_3$;
$R_8$ is $R_3$, $R_3CO$, or $R_3SO_2$; and $R_9$ is a straight, branched, or cyclic alkyl group of from $C_1$ to $C_{12}$.

The compounds of the present invention inhibit ethylene production in plant material, for example, strips of cucumber cotyledons and germinating squash seeds. In addition, 2,3-methaneproline and its derivatives are useful in the modification of biologically active compounds.

The compounds of the present invention have a significantly different structure than and exhibit significantly different properties from the cyclopropyl amino acids known to date. 2,3-methanoproline cannot exist in a chair conformation, as does 3,4-methanoproline. Further, the cyclopropyl group in 2,3-methanoproline may act as a suicide substrate for enzymes which catalyze reactions in the area of the amide bonds of the peptide. This enzyme inactivation route is unavailable in 3,4-methanoproline, because the cyclopropyl group is bound at the $C_\alpha$-$C_\gamma$ position.

Figure 1:
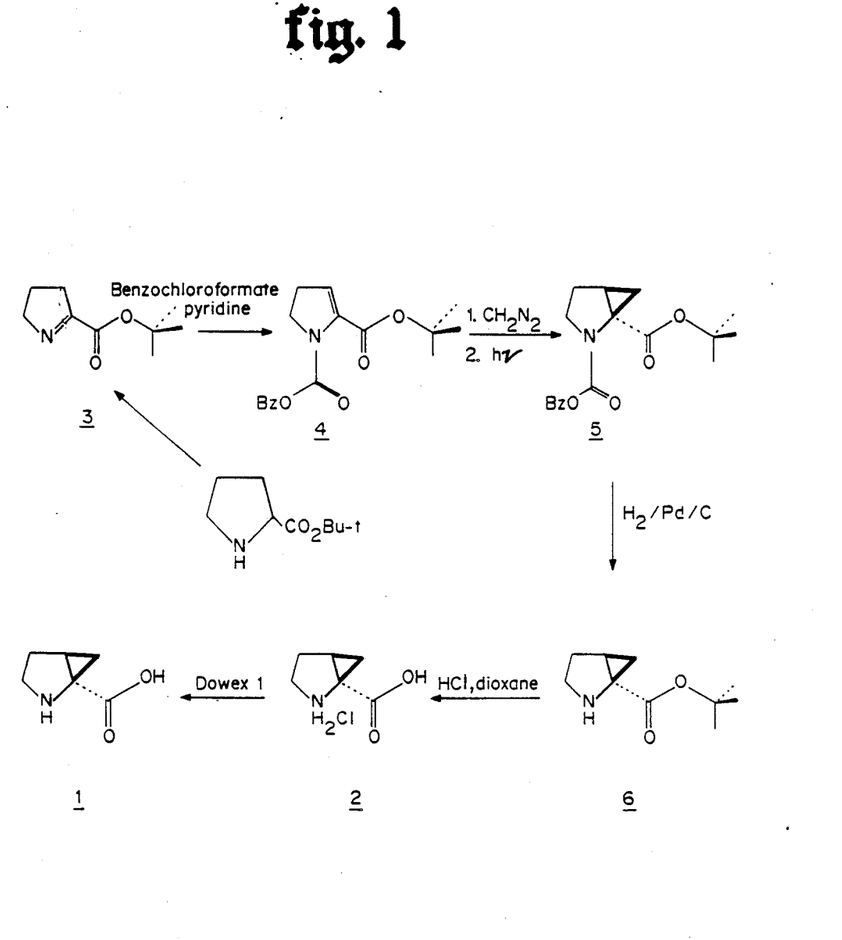
FIG. 1 is an illustration of Scheme 1 for the synthesis of 2,3-methanoproline or its derivatives in which a diazo compound is reacted with a derivative of 2,3-dehydroproline to form a proline derivative, in accordance with the present invention.
Figure 2:
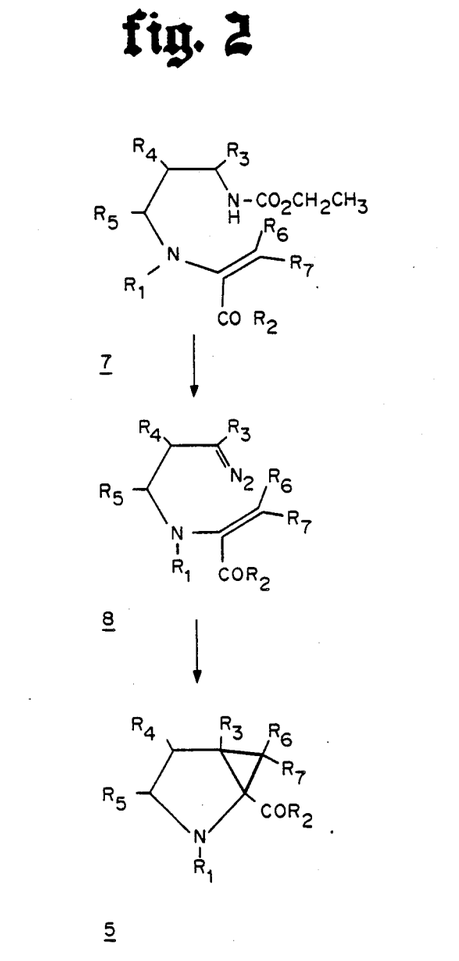
FIG. 2 is an illustration of Scheme 2 for the synthesis of 2,3-methanoproline or its derivatives in which an N-diazoalkyl dehydroalanine derivative is cyclized intramolecularly, and then pyrolyzed or photolyzed to form a proline derivative, in accordance with the present invention.

The compounds having the general structure set forth above may be made by a variety of methods, including reacting a diazo compound with a derivative of 2,3-dehydroproline (Scheme 1) or intramolecular cyclization of an N-diazoalkyl dehydroalanine derivative followed by pyrolysis or photolysis (Scheme 2).

Scheme 1

A first method of synthesis of 2,3-methanoproline and its derivatives, referred to herein as Scheme 1, is illustrated in FIG. 1. In step 1 of Scheme 1, the alkyl or aryl ester of proline (2) is oxidized to the corresponding 1,2-dehydroproline ester (alkyl or aryl 1,2-dehydro-pyrrolidine-2-carboxylate) (3). This reaction may be accomplished with a variety of oxidizing reagents, for example, tert-butylhypochlorite, sodium hypochlorite, manganese dioxide, mercuric oxide and other mild oxidizing agents. The reaction is done in an organic solvent, for example, ether, methylene chloride, chloroform, ethyl acetate, dimethyl formamide, or acetonitrile, at −50° C. to 80° C. When tert-butylhypochlorite is used, after the reaction is completed, the reaction mixture is stirred with an excess of triethylamine to eliminate hydrogen chloride, giving a 1,2-dehydroproline ester.

In the second step of Scheme 1, the ester of 1,2-dehydroproline (3) is reacted with benzyl chloroformate in the presence of a tertiary amine such as triethylamine or pyridine to produce the ester of N-carbobenzyloxy-2,3-dehydroproline (alkyl or aryl N-carbobenzyloxy-2,3-dehydro-pyrrolidine-2-carboxylate) (4). This reaction is conducted at a temperature range from 50° C. to 50° C. in organic solvents such as ether, methylene chloride, acetonitrile or ethyl acetate. Suitable substitutes for benzyl chloroformate include t-butoxycarbonyl chloride, p-methoxy- or p-nitro-benzyloxycarbonyl chloride, or acetyl or benzoyl chloride.

In the third step of Scheme 1, alkyl or aryl N-carbobenzyloxy-2,3-dehydro-pyrrolidine-2-carboxylate (4) is reacted with diazomethane or a substituted diazomethane to produce the alkyl or aryl ester of N-carbobenzyloxy-2,3-methanopyrrolidine-2-carboxylate (5). The substituents on the carbon atom of diazomethane determine the substituents $R_6$ and $R_7$ in the proline derivative of the present invention. Diazomethane or a substituted diazomethane is generated under nitrogen in situ, by methods generally known to those skilled in the art, for example, as described in M. Hudlicky, *J. Org. Chem.* 45, 5377 (1980), incorporated herein by reference.

The N-carbobenzyloxy group is then removed from compound (5) by reduction with $H_2$ and palladium on carbon as the catalyst, or, alternatively, using trifluoroacetic acid with thioanisole or hydrogen bromide in acetic acid.

The alkyl or aryl ester of the 2,3-methanopyrrolidine-2-carboxylate (5) may then be removed by acidic or basic hydrolysis to form the target compound, 2,3-methanoproline (1). If an acid such as HCl is used to remove the ester, the corresponding ammonium salt is formed. The free base may be generated by, for example, passing a solution of the compound through a basic ionic exchange resin. Alternatively, it may be removed by treatment with a basic solution followed by acidification to the isoelectric point.

Derivatives of 2,3-methanopyrrolidine-2-carboxylic acid having N-acyl groups other than benzyloxycarbonyl in the $R_1$ position are prepared by reacting compound (3) with $ClCO_2R_3$ or acetyl or benzoyl chloride, and then proceeding with the synthetic steps described above. Alternatively, 2,3-methanoproline may be reacted with an alkyl halide to produce the corresponding N-alkyl-2,3-methanoproline. This reaction occurs by simply mixing the alkyl halide with compound (1) at room temperature or if necessary in the presence of a base such as potassium carbonate. The $R_1$ sulfonamide derivative may be prepared by reacting an $ArSO_2Cl$ or $R_9SO_2Cl$ with compound (6). The carboxylic acid ester is then removed by treatment with an alkali solution.

Derivatives of 2,3-methanoproline which have a halogen (Cl, Br, F, I) in the $R_2$ position may be prepared by reacting the N-acyl 2,3-methanoproline derivative with thionyl chloride, phosphorous trichloride, phosphorous pentachloride, phosphorous tribromide, or phosphorous triiodide. This reaction may be performed in chloroform, methylene chloride, or other common organic solvents, in a temperature range of 0° to 80° C. The acid chloride produced may be reacted with ammonia or an amine to produce the corresponding amide. Desired alkyl or aryl esters of 2,3-methanoproline may be prepared by reacting the N-acyl 2,3-methanoproline acid halide derivative with the desired alcohol or phenol, according to procedures known to those skilled in the art.

In a variation of Scheme 1, an ester of pyroglutamic acid may be substituted for the ester of pyrrolidine-2-carboxylate (2) in the first step of the reaction sequence. The remaining steps of the synthetic scheme may be carried out as described above.

When the compounds of the present invention are prepared from pyroglutamic acid, the final product, as well as the intermediates, have a carbonyl group in the R5 position. An advantage of this procedure to prepare the compounds of the present invention is that pyroglutamic acid is an inexpensive starting material, well suited for commercial scale reactions. Reduction of the carbonyl group by methods known to those skilled in the art, for example, as described in K. Dranz, et al., *J. Org. Chem.* 57, 3494 (1986), provides compound (1) or a derivative thereof.

The chemical reactions described for Scheme 1 and Scheme 2 are generally disclosed in terms of their broadest application for the preparation of the compounds of this invention. Modifications of the general methods may be required in the synthesis of some compounds using techniques known to those skilled in the art, for example, by appropriate protection of interfering groups, by changing to alternative conventional reactions, by routine modification of reaction conditions, or other reactions disclosed herein or otherwise conventional. In all preparative methods, all starting materials are known or are readily prepared from known starting materials.

The following specific working examples of Scheme 1 are, therefore, to be construed as merely illustrative, and are not intended to limit the disclosure in any way.

t-Butyl 1,2-dehydropyrrolidine-2-carboxylate (3)

To 100 ml of ether at −20° C. were added simultaneously t-butyl pyrrolidine-2-carboxylate (6.8 g, 4.0 mmol) and freshly prepared tert-butyl-hypochlorite (4.8 ml, 40 mmol) dropwise over a 15 minute period. The cold bath was then removed and the mixture was stirred for 30 minutes after which triethylamine (5.6 ml, 40 mmol) was added. A white precipitate quickly formed and the suspension was stirred at room temperature for 40 hours. The precipitate was filtered and washed with ether (2×50 ml). The filtrate was concentrated and the residue was distilled with a Kuglerohr apparatus to give compound (3) (6.0 g, 89%) as a colorless oil: bp=55°-70°/0.3 torr. $^1$H NMR (CDCl$_3$): 3.9-4.2 (m, 2H), 2.6-2.9 (m, 2H), 1.8-2.1 (m, 2H), 1.52 (s, 9H) ppm.

t-Butyl N-carbobenzyloxy-2,3-dehydropyrrolidine-2-carboxylate (4)

To a stirred solution of compound (3) (16.0 g, 94.8 mmol) and pyridine (12 ml, 150 mmol) in CH$_2$Cl$_2$ (100 ml) at −20° C. was added benzyl chloroformate (21.4 ml, 150 mmol) dropwise over a 15 minute period. The solution was stirred at room temperature overnight. N,N-Diethylethylenediamine (14 ml, 100 mmol) was then added dropwise over 15 minutes to destroy the excess chloroformate and the reaction was stirred for an additional 2 hours. The solution was then diluted with CH$_2$Cl$_2$ (300 ml) and washed with 10% aqueous citric acid (2×300 ml) and 10% aqueous Na$_2$CO$_3$ (300 ml). The organic phase was dried (K$_2$CO$_3$), concentrated, and chromatographed on silica gel (230-400 mesh, 65×270 mm column, 3 portions, hexanes to 6:4 hexanes-/ethyl acetate gradient elution) to produce 22.4 g (78%) of compound (4) as a colorless oil; $^1$H NMR (CDCl$_3$): δ7.21 (s, 5H), 5.68 (t, 1H, J=3 Hz), 5.08 (s, 2H) 3.91 (t, 2H, J+Hz), 2.57 (d of t, 2H, J=9 Hz, J=Hz), 1.40 (s, 9H) ppm; $^{13}$C NMR (CDCl$_3$): δ160 1.8, 153.4, 137.6, 36.0, 128.3, 128.0, 119.1, 81.8, 67.3, 48.6, 28.3, 27.8 ppm.

t-Butyl N-carbobenzyloxy-2,3-methanopyrrolidine-2-carboxylate (5)

Compound (4) (24.0 g, 79.2 mmol) was divided into three equal portions and each portion was treated with excess diazomethane. Each batch of diazomethane was generated under nitrogen from N-methyl-N-nitroso-para-toluenesulphonamide (Diazald, 32 g, 150 mmol) by methods known to those skilled in the art, as, for example, described by M. Hudlicky, *J. Org. Chem.* 45, 5377 (1980). The resulting diazomethane/ether mixture was collected with a Dry Ice/CCl$_4$ cooled condenser and added directly to a Dry Ice/CCl$_4$ cooled solution of compound (4) in CH$_2$Cl$_2$ (100 ml). This solution was then stirred at room temperature for 24 hours after which CaCl$_2$ (10-20 g) was added and stirring was continued for 16 hours. The CaCl$_2$ was filtered to give a colorless solution of crude pyrazoline which was concentrated and photolyzed for 4 hours in CH$_2$Cl$_2$ (500 ml) in an ice-water cooled apparatus using a 450 W Hanovia medium-pressure mercury lamp. The crude 2,3-methanopyrrolidine from these three runs was then chromatographed in two portions on silica gel (230-400 mesh, 65×270 mm column, hexanes to 1:1 hexanes-/ethyl acetate gradient elution) to afford 16.4 g (65%) of compound (5) as a colorless oil; $^1$H NMR (CDCl$_3$) δ7.21 (s, 5H), 5.07 (s, 2H), 3.4-4.1 (m, 2H), 1.6-2.4 (m, 4H), 1.47 (s, 9H), 0.97 (br s, 1H) ppm; $^{13}$C NMR (CDCl$_3$): δ169.5, 155.7, 136.54, 128.2, 127.5, 80.9, 66.8, 51.4 (br), 48.2, 30.5 (br), 27.7, 26.5, 26.0 (br) ppm.

t-Butyl 2,3-Methanopyrrolidine-2-carboxylate (6)

Compound (5) was dissolved in ethyl acetate (300 ml) and the solution was flushed with argon. Palladium-on-carbon (5%, 3 g) was added and hydrogen was bubbled into the stirred suspension until no starting material remained (2 hours as indicated by TLC). The flask was then flushed with nitrogen and the catalyst was removed by filtration. The catalyst was washed with methanol (3×100 ml) and the combined filtrates were concentrated. The residue was then distilled with a Kuglerohr apparatus at reduced pressure to give 6.6 g (85%) of compound (6) as a light yellow oil: bp=90°-120° C./0.8 mm; $^1$H NMR (C$_6$D$_6$): δ2.83 (m, 1H), 2.32 (m, 1H), 2.10 (br s, 1H), 1.76 (m, 1H), 1.3-1.65 (m, 3H), 1.36 (s, 9H), 0.85 (t, J=6 Hz) ppm. $^{13}$NMR (C$_6$D$_6$) δ172.2 (C=O), 80.1 (quat), 50.1 (quat), 44.3 (CH$_2$), 28.1 (CH$_2$), 27.7 (CH), 16.7 (CH$_2$) ppm.

2,3-Methanopyrrolidine-2-carboxylic acid (1) (2,3-Methanoproline)

Distilled compound (6) (4.4 g, 24 mmol) and anisole (3.0 ml, 28 mmol) were dissolved in 3.0 M HCl in dioxane (40 ml) and the solution was stirred at room temperature overnight. A white precipitate formed. The suspension was diluted with hexanes (200 ml). The precipitate was filtered and washed with ether (2×100 ml). The solid was then dissolved in isopropanol (100 ml) and reprecipitated with ether (800 ml) to give a light orange solid which was chromatographed on reverse-phase silica gel (10 g, 40 um flash chromatography grade C$_{18}$, water). The aqueous solution was then lyophilized and the yellow-white solid was recrystallized from isopropanol/ether. After the initial precipitation of a small amount of highly colored material, the amino acid hydrochloride hydrate (compound (2), 3.2 g, 73%) was isolated as granular white crystals: mp=200°-215° C.; $^{13}$C NMR (D$_2$O): δ171.5, 46.7, 43.2, 27.0, 24.6, 14.9 ppm; MS:m/e 127 (M+),109 (M—H$_2$O).

Anal. Calcd. for C$_6$H$_9$NO$_2$.HCl.H$_2$O: C, 39.67%; H, 6.66%; N, 7.74%. Found: C, 39.73%; H, 6.72%; N, 7.68%.

The zwitterion of (1) was prepared from its hydrochloride salt by stirring an aqueous solution of the salt with Dowex 1X8-50-acetate (50 g) overnight at room temperature. The resin was removed by filtration and washed with water (3×100 ml). The combined filtrates were lyophilized to afford the desired zwitterion (1 7 g, 53% from compound (6)) as a white powder: mp=197°-203° C.; $^1$H NMR (D$_2$O): δ3.58 (m, 1H), 3.06 (m, 1H), 2.1-2.5 (m, 3H), 1.3-1.8 (m, 2H) ppm; $^{13}$C NMR (D$_2$O): δ173.9, 48.8, 41.2, 24.8, 13.2 ppm.

Anal. Calcd. for C$_6$H$_9$NO$_2$·¼ H$_2$O: C, 54.72%; H, 6.89%; N, 10.68%. Found: C, 54.6%; H, 7.30%; N, 10.55%.

Scheme 2

A second method of synthesis of 2,3-methanoproline and its derivatives, referred to herein as Scheme 2, is illustrated in FIG. 2. The N-alkylated dehydroalanine derivative (7) is prepared by N-alkylation of a dehydroalanine derivative using an appropriate alkyl halide in acetone and powdered potassium carbonate. Treatment of (7) with nitrous acid followed by a strong base generates the diazo compound (8) which spontaneously cyclizes to a pyrazoline which is then photolyzed without isolation to give the cyclopropane (6). This is then converted into 2,3-methanoproline by procedures described in Scheme 1 or other methods known to those skilled in the art. The following example is merely illustrative of the method of Scheme 2, and is not meant to limit the scope of the invention.

t-Butyl-N-benzyloxycarbonyl-2,3-methanopyrrolidine (5)

A suspension of 3 mmole of compound (7) in 25 ml of water is treated with 1.1 equivalents of solid sodium nitrite followed by 5–10 mL of acetic acid. Ether (100 ml) is added and the nitroso compound is extracted into the organic layer. After separation of the phases, the aqueous phase is extracted twice with 50 ml of ether. The combined extracts are dried over anhydrous sodium sulfate, filtered and the filtrate is evaporated to dryness. The crude nitroso compound is dissolved in 25 ml of methanol containing 3 mmole of sodium methoxide. The colored solution of diazo compound is stirred for two hours or until it has become colorless and the solution is evaporated to dryness. The crude pyrazoline is dissolved in 500 ml of methylene chloride followed by photolysis using a 450 watt Hanovia medium pressure lamp for 4 hr at room temperature or below. The resulting solution is evaporated in vacuo and the product (5) is isolated. Its physical properties are identical to samples of (5) as prepared in Scheme 1.

The following examples illustrate the use of the compounds of the present invention to inhibit ethylene production in plant material and to modify biologically active molecules.

EXAMPLE 1

Inhibition of Ethylene Production in Plant Material

An aspect of the present invention is the use of the compounds of the present invention to inhibit ethylene production in plant material.

Ethylene is a hormone that plays a variety of roles in the life of a normal plant, most of which are tied to plant aging. For example, ethylene is involved in leaf abscission and lateral bud inhibition. One of the most important roles of ethylene is the stimulation of fruit ripening. Once the ovary of the flower (which forms the fruit) has passed through an early cell division stage followed by a growth stage, and has attained its maximum size, a variety of chemical changes begin which cause the fruit to ripen. This ripening process starts with a sudden sharp increase in $CO_2$ output, followed shortly by a sharp decline in $CO_2$ output. It can be shown that the dispersed metabolic activity, called the climacteric, is triggered by an approximately hundredfold increase in the concentration of ethylene. Inhibition of ethylene production, or removal of the ethylene as fast as the fruit produces it, prevents the climacteric, and no ripening occurs.

Concentrations as low as 100 ppm 2,3-methanoproline reduced ethylene production from strips of cucumber cotyledons and whole germinating squash seeds (Table 1). Specifically, a concentration of 100 ppm of compound (1) inhibited ethylene production by an average of 22% and 30% in cucumber cotyledon strips and germinating squash seeds, respectively, while the 1,000 ppm solution inhibited ethylene by 36% and 40% in the same respective tissue. On average, ethylene production was inhibited 26% and 38% by the 100 and 1,000 ppm solutions of 2,3-methanoproline, respectively.

Ethylene production from strips of cucumber cotyledons was inhibited about 50% by the 10,000 ppm solution. Inhibition was roughly linear on a log scale; each 10-fold increase in concentration resulted in an approximately 12% reduction in ethylene production (approx. 28%, 38%, and 50% reductions for 100, 1,000, and 10,000 ppm, respectively).

The compound was not found to inhibit ethylene production in apple cortex, carrot cortex, whole cucumber cotyledons, or excised squash roots.

Strips of cucumber cotyledons were used to test the effect of (±) 2,3-methanoproline on the activity of the ethylene forming enzyme (EFE). Addition of 0.5 mM ACC (1-aminocyclopropane carboxylic acid, the precursor to ethylene in plants) stimulated ethylene production over 70-fold in the control tissue, but only 11-fold in treated tissue this indicates that 2,3-methanoproline probably inhibits conversion of ACC to ethylene through an effect on the EFE.

Preparation of the solutions. Fresh aqueous solutions were prepared for each experiment. The solutions were made by diluting 10,000 and 100 ppm (wt/wt) stock solutions.

Cucumber cotyledons. Cucumber seedlings (*Cucumis sativus* L. cv. Poinsett 76) were germinated in vermiculite for about one week at 20° under fluorescent light. Only fully expanded cotyledons were used. They were excised from the hypocotyl with a razor blade and a 20 ul drop was applied to the base of each cotyledon. Two cotyledons were enclosed in a 15 ml glass test tube after the solution had been absorbed, and ethylene was analyzed from headspace gas samples taken after from 1 to 5 hr of incubation.

Cotyledons were cut into 3 mm thick longitudinal slices to increase absorption of the solutions. Sixty ul of each solution was applied to approximately 9 strips. Excess solution was removed after 2 hr. Ethylene production was monitored by enclosing the slices in 15-ml glass test tubes, and testing the enclosed air for ethylene by flame ionization gas chromatography (Table 1).

Ethylene forming enzyme (EFE) activity was assayed using strips of cucumber cotyledons. The strips (0.1 g) were treated with 80 ul of water or 10,000 ppm ACC 309,270 for 2 hr, then with 80 ul of water or 0.5 mM ACC for 16 hr, then blotted dry. The ethylene concentration measured in 1-ml gas samples taken from the sealed test tube after 6 hr incubation at 20° C.

Germinatinq squash seeds. Seeds of Table King Acorn squash were germinated on moist filter paper for either 3 or 5 days at 20°. Three uniform seeds were placed into 15-ml glass test tubes with 40 ul of various concentrations. The tubes were capped after 3 hr and ethylene production determined by flame ionization gas chromatography.

TABLE 1

Inhibition of Ethylene production (nl/g hr) by 2,3-Methanoproline*.

| Concentration of Inhibitor (ppm) | Cucumber cotyledons | | | Germinating squash seeds | |
|---|---|---|---|---|---|
| | Strips | Strips | Whole | 3 days | 5 days |
| 0 | 1.40$^a$ | 1.65$^a$ | 2.08 | 5.33$^a$ | 2.86$^a$ |
| 10 | | | | 4.72$^b$ | 2.62$^a$ |
| 100 | 1.03$^b$ | 1.35$^b$ | 2.39 | 3.61$^c$ | 2.12$^b$ |
| 1,100 | 0.67$^c$ | 1.29$^b$ | 2.60 | 3.10$^d$ | 1.85$^c$ |
| 10,000 | 0.36$^d$ | 1.14$^c$ | 2.76 | | |

*Means followed by the same letter are not significantly different at the 5% level.

EXAMPLE 2

Modification of Biologically Active Molecules

Another aspect of the present invention is the modification of biologically active molecules by the incorporation of the compounds of the present invention.

These compounds may be substituted for naturally occurring proline or may by substituted for other amino acids in biologically active molecule to be modified, such as peptides, glycoproteins, metalloproteins, protein conjugates, and lipoproteins.

For example, 2,3-methanoproline and its derivatives thereof according to the present invention may be substituted for natural proline or one or more of the other amino acids in angiotensinogen, described in the Backround of The Invention, to form a synthetic angiotensinogen analog. In the same way, the compounds of the present invention may be incorporated into AI or AII to prepare a modified AI or AII peptide.

Alternatively, analogs of ACE inhibitors such as capoten, vasotec, and lysinopril may be prepared by the substitution of 2,3-methanoproline or its derivatives for the proline residues in these compounds.

Similarly, the proline derivatives of the present invention may be substituted for one or more of the proline residues or one or more of the other amino acids in bradykinin, Arg-Pro-Pro-Gly-Phe-Ser-Pro-Phe-Arg, to form a synthetic analog of this important biologically active peptide.

In the same way, the proline derivatives of the present invention may be substituted for naturally occurring proline or other amino acids in thyrotropin releasing hormone (TRH) (Glp-His-Pro), melanocyte inhibiting factor (Pro-Leu-Gly), and tuftsin (Thre-Lys-Pro-Arg).

The present invention is not limited to modification of the above described biologically active molecules. Given the description of this invention, it is obvious to one skilled in the art how to prepare synthetic analogs of other biologically active molecules.

For example, methods of preparation of peptides from amino acids are known to those skilled in the art and are described in many standard texts, for example, M. Bodanszky and A. Bodanszky, "The Practice of Peptide Synthesis", Springer-Verlag, Berlin (1984), incorporated herein by reference. See also U.S. Pat. No. 4,629,784 "Synthesis of Cyclopropane Amino Acids" issued to Stammer on Dec. 16, 1986.

Methods for testing the biological activity of molecules modified as described herein for enzymatic stability and altered conformation are known to those skilled in the art.

For example, molecules may be tested for their effect on enzymes using standard Michalis-Menten kinetics. The use of Michalis-Menton kinetics to determine the effect of a substrate on a receptor or enzyme is found in many standard texts, for example, Lehninger, *Principles of Biochemistry*, Chapter 1 (Worth Publishers, Inc. (1982)).

There are two types of enzyme inhibitors, irreversible and reversible. Irreversible inhibitors are those which combine with or destroy a functional group on the enzyme molecule that is necessary for its catalytic activity. A Michalis-Menton plot of an enzymic reaction in the presence of an irreversible inhibitor will exhibit a rapid decrease in enzymatic activity without regeneration of enzymatic activity after removal of the inhibitor.

A reversible inhibitor is classified as either competitive or noncompetitive. A competitive inhibitor competes with the substrate for binding to the active site but, once bound, cannot be transformed by the enzyme. In noncompetitive inhibition, the inhibitor binds at a site on the enzyme other than at the substrate binding site, altering the conformation of the enzyme molecule so that reversible inactivation occurs.

Double reciprocal Michalis-Menton plots of enzyme data offer a convenient way of determining whether an enzyme inhibitor is competitive or noncompetitive. Two sets of rate experiments are performed. In the first experiment, the enzyme and substrate concentration are held constant and the effect of increasing the inhibitor concentration on the initial rate vo is determined. In the second experiment, the enzyme and inhibitor concentration are kept constant, and the substrate concentration is varied. The reciprocal 1/$v_o$ is plotted against the reciprocal 1/s of the substrate concentration. Competitive inhibitors yield a series of lines with differing slopes but a common intercept on the y-axis. Noncompetitive inhibitors provide a series of lines that have differing slopes and no common y-intercept.

Another method of determining whether and how a proline-modified biologically active molecule of the present invention binds to a receptor or enzyme is to analyze the complex by x-ray crystallography. Alternatively, those having ordinary skill in the art will know how to utilize infrared, ultraviolet, and nuclear magnetic resonance spectroscopy to gain information about complexes of substrates prepared according the methods of the present invention. For example, see generally, Cantor and Schimmel, *Biophysical Chemistry* Parts I, II and III (W. H. Freeman and Company, New York (1980)), incorporated herein by reference.

This invention has been described with reference to its preferred embodiments. Variations and modifications of the present invention will be obvious to one of ordinary skill in the art from the foregoing detailed description of the invention. It is intended that all these variations and modifications be included within the scope of the appended claims.

We claim:

1. A compound of the general structure wherein:

$R_1$ is H, $R_9$, $COR_3$, $CO_2R_3$, $SO_2R_3$, or $R_3CH(NH_2)CO-$;

$R_2$ is H, $R_9$, $OR_3$, OH, Cl, Br, F, I, $NH_2$, $NHR_3$, $N(R_3)_2$, benzyl, phenyl, or substituted benzyl or phenyl wherein the substituents are selected from the group consisting of F, Cl, Br, I, $R_9$, $OR_9$, $NHR_9$, $N(R_9)_2$, $SR_9$, $SO_2R_9$, $COR_9$, or $CO_2R_9$;

$R_3$ is H, $R_9$, phenyl or substituted phenyl wherein the substituents are selected from the group consisting of F, Cl, Br, I, $R_9$, $OR_9$, $NHR_9$, $N(R_9)_2$, $SR_9$, $SO_2R_9$, $COR_9$, $CO_2R_9$;

$R_4$ is H, Cl, Br, I, F, $OR_8$ or OH;

$R_5$ is $R_3$ or =O;

$R_6$ and $R_7$ are $R_3$ or $COR_3$;

$R_8$ is $R_3$, $R_3CO$, or $R_3SO_2$; and

$R_9$ is a straight, branched, or cyclic alkyl group of from $C_1$ to $C_{12}$.

2. The compound of claim 1, wherein $R_1$, $R_3$, $R_4$, $R_5$, $R_6$, and $R_7$ are H, and $R_2$ is OH.

3. The compound of claim 1 wherein $R_1$ is:

4. The compound of claim 1 wherein $R_1$ is:

5. The compound of claim 1 wherein $R_1$ is:

6. The compound of claim 1 wherein $R_1$ is:

7. A method of inhibiting ethylene production in plant material comprising administering in a botanically acceptable carrier the compound of the general structure wherein:
$R_1$ is H, $R_9$, $COR_3$, $CO_2R_3$, $SO_2R_3$, or $R_3CH(NH_2)CO-$;

$R_2$ is H, $R_9$, $OR_3$, OH, Cl, Br, F, I, $NH_2$, $NHR_3$, $N(R_3)_2$, benzyl, phenyl, or substituted benzyl or phenyl wherein the substituents are selected from the group consisting of F, Cl, Br, I, $R_9$, $OR_9$, $NHR_9$, $N(R_9)_2$, $SR_9$, $SO_2R_9$, $COR_9$, or $CO_2R_9$;

$R_3$ is H, $R_9$, phenyl or substituted phenyl wherein the substituents are selected from the group consisting of F, Cl, Br, I, $R_9$, $OR_9$, $NHR_9$, $N(R_9)_2$, $SR_9$, $SO_2R_9$, $COR_9$, $CO_2R_9$;

$R_4$ is H, Cl, Br, I, F, $OR_8$ or OH;

$R_5$ is $R_3$ or =O;

$R_6$ and $R_7$ are $R_3$ or $COR_3$;

$R_8$ is $R_3$, $R_3CO$, or $R_3SO_2$; and $R_9$ is straight, branched, or cyclic alkyl group of from $C_1$ to $C_{12}$.

* * * * *